United States Patent [19]

Howard, Jr. et al.

[11] Patent Number: 4,476,307

[45] Date of Patent: Oct. 9, 1984

[54] HETEROYLIDENE INDOLONE COMPOUNDS

[75] Inventors: Harry R. Howard, Jr., Bristol; Reinhard Sarges, Mystic, both of Conn.

[73] Assignee: Pfizer Inc., New York, N.Y.

[21] Appl. No.: 420,544

[22] Filed: Sep. 20, 1982

[51] Int. Cl.$^3$ ................. C07D 401/04; C07D 403/04
[52] U.S. Cl. .................................. 546/201; 548/466; 260/245.7
[58] Field of Search ................. 548/466; 546/201; 260/245.7

[56] References Cited

U.S. PATENT DOCUMENTS 3,506,683  4/1970  Anthony et al. ............... 548/466

FOREIGN PATENT DOCUMENTS 849626  6/1977  Belgium .

*Primary Examiner*—Robert W. Ramsuer
*Attorney, Agent, or Firm*—Charles J. Knuth; Albert E. Frost; Robert K. Blackwood

[57] ABSTRACT

Certain substituted 1-phenyl-3-(aminoalkylidene)-2(1H,3H)-indolones are highly potent gabaergic agents, valuable in the treatment of individuals suffering from schizophrenia or reversing the side effects of a previously or concurrently administered neuroleptic agent; or in the treatment of epilepsy. A wider class of substituted 1-phenyl-3-(aminoalkylidene)-2(1H,3H)-indolones, together with 1-phenyl-3-(2-pyrrolidinylidene)-2(1H,3H)-indolones, and homologs thereof, are valuable in the treatment of anxiety.

11 Claims, No Drawings

HETEROYLIDENE INDOLONE COMPOUNDS

BACKGROUND OF THE INVENTION

Certain novel, 1-phenyl-3-[aminoalkylidene or di(-loweralkyl)aminoalkylidene]-2-(1H,3H)-indolones, specifically substituted on phenyl with at least one alkyl, alkoxy, alkylthio, chloro, fluoro or trifluoromethyl group, are potent gabaergic agents, valuable in the treatment of schizophrenia per se, as well as in reversing or avoiding side effect of oral-facial dyskinesia (tardive dyskinesia), commonly seen in schizophrenic individuals under present or past treatment with a neuroleptic agent. The present invention encompasses these novel gabaergic agents, together with pharmaceutical compositions thereof, and use thereof in treating schizophrenia or reversing the side effects of a previously or concurrently administered neuroleptic agent. Most of these compounds also have valuable anxiolytic activity, as detailed below.

More broadly, the present invention encompasses variously substituted 1-phenyl-3-[aminoalkylidene-, lower alkylaminoalkylidene- and di(loweralkyl)aminoalkylidene]-2-(1H,3H)-indolones (some of which are known compounds), novel 1-phenyl-3-(piperidino-, pyrrolidino-, morpholino- or imidazolo- alkylidene)-2-(1H,3H)-indolones and novel 1-phenyl-3-(2-pyrrolidinylidene, 2-piperidinylidene, or 2-perhydroazepinylidene, optionally substituted on nitrogen with lower alkyl, phenyl or benzyl)-2(1H,3H)-indolones. These three classes of compounds are anxiolytic agents, valuable in the treatment of hyperanxious individuals. The present invention is thus also directed to the above two novel classes of compounds and pharmaceutical compositions thereof, and to the use of all three classes of compounds in the treatment of anxiety in hyperanxious individuals.

Belgian Pat. No. 849,626 broadly discloses compounds of the formula

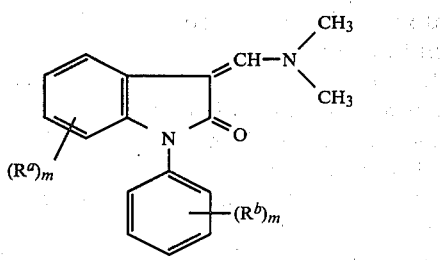

which include m as 1, 2 or 3 and $R^a$ and $R^b$ each as H, OH, lower alkyl, lower alkoxy, F, Cl, Br, $NO_2$, $NH_2$ or $C_6H_5CH_2$.

These compounds are not disclosed as having pharmaceutical utility per se, but rather are indicated to be chemical intermediates. The only compounds of this class isolated and characterized are the two compounds wherein $R^a$=H and $R^b$=3-methoxy; and the latter compound, like at least two dozen other compounds of this class, does not possess MPA (3-mercaptopropionic acid) induced convulsion inhibitory activity ("gabaergic" activity). However, from among the many thousands of possible compounds defined by the Belgian patent, we have surprisingly found that a few, defined by the formula (I) below have gabaergic activity and so are useful in the treatment of schizophrenic individuals.

SUMMARY OF THE INVENTION

The present invention is concerned in part with compounds of the formula

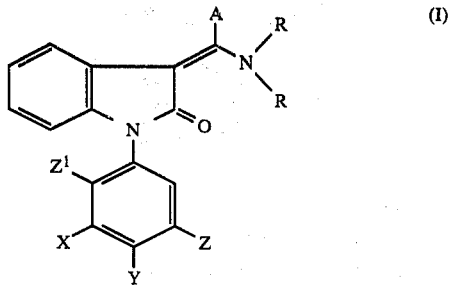

wherein:
- A is hydrogen or methyl;
- R is hydrogen or ($C_1$–$C_2$)alkyl;
- X is hydrogen ($C_1$–$C_2$)alkyl ($C_1$–$C_2$) alkoxy, ($C_1$–$C_2$)alkylthio; chloro, fluoro or trifluoromethyl;
- Y is hydrogen, ($C_1$–$C_2$)alkyl, ($C_1$–$C_2$)alkoxy or ($C_1$–$C_2$)alkylthio; and
- Z and $Z^1$ are each independently hydrogen or methyl;

with the provisos that:
- at least one of X, Y, Z and $Z^1$ is other than hydrogen; and
- at least one of X and Y is other than ($C_1$–$C_2$)-alkoxy.

Based on their excellent gabaergic activity as well as ease of preparation, one group of preferred compounds of the formula (I) have Z and $Z^1$ as hydrogen, with X as chloro and Y as hydrogen. The most preferred compounds in this subclass have A as hydrogen, with R as hydrogen, methyl or ethyl, or both A and R as methyl. A second group of preferred compounds of the formula (I) not only have Z and $Z^1$ as hydrogen, but also A and Y as hydrogen. The most preferred compounds in this subclass have X as ($C_1$–$C_2$)alkyl, trifluoromethyl, methoxy or fluoro. A third subclass of preferred compounds also have Z and $Z^1$ as hydrogen, with R as methyl and Y as methoxy. Preferred compounds in this subclass have X as chloro with A as hydrogen or methyl, or X as fluoro with A as hydrogen. In the two additional most preferred compounds, one has A and $Z^1$ as hydrogen, R and Z as methyl, X as chloro and Y as methoxy; and the other has A, X, Y and Z as hydrogen, and R and $Z^1$ as methyl.

The present invention also encompasses pharmaceutical compositions suitable for the treatment of a person suffering from schizophrenia which comprise a pharmaceutically-acceptable carrier and a compound of the formula (I) in an amount which will alleviate said schizophrenia or reverse the side effects of a neuroleptic agent simultaneously or previously administered in the treatment of said schizophrenia; and a method of treating a person suffering from schizophrenia which comprises administration to said person a compound of the formula (I) in an amount sufficient to alleviate said schizophrenia or reverse the side effects of a neuroleptic agent simultaneously or previously used in the treatment of said schizophrenia.

The present invention also encompasses compounds of the formula

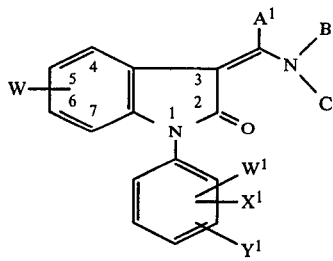 (II)

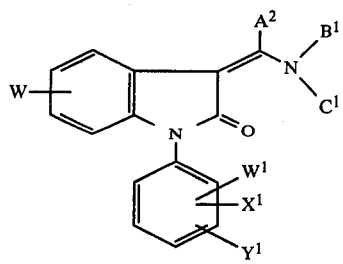 (III)

wherein,
in a first alternative,
A¹ is hydrogen or methy; and
B and C together with the nitrogen atom to which they are attached, form a piperidine, pyrrolidine, morpholine or imidazole ring; or
in a second alternative,
A¹ and B together are 1,3-propylene, 1,4-butylene or 1,5-pentylene; and C is hydrogen, $(C_1-C_2)$alkyl, phenyl or benzyl;
W is hydrogen, $(C_1-C_2)$alkyl, $(C_1-C_2)$alkoxy chloro or fluoro; and
$W^1$, $X^1$ and $Y^1$ are each independently hydrogen, $(C_1-C_2)$alkyl, $(C_1-C_2)$alkoxy, $(C_1-C_2)$alkylthio, bromo, chloro, fluoro, trifluoromethyl, hydroxy, formyl, carboxamido, $(C_1-C_2)$alkylcarboxamido, di$(C_1-C_2)$alkylcarboxamido, cyano, nitro, amino, $(C_1-C_2)$alkylamino or di$(C_1-C_2)$alkylamino.

Based on their excellent anxiolytic activity, as well as their ease of preparation, preferred compounds of the formula (II) wherein A¹, B and C are in the first alternative have A¹, W, W¹ and Y¹ as hydrogen. A first more preferred group has, X¹ as chloro. Most preferred compounds in this subclass are those wherein B and C taken together with the nitrogen to which they are attached, form either a pyrrolidine or a morpholine ring. A second more preferred group have X¹ as hydrogen, most preferably those wherein B and C taken together with the nitrogen to which they are attached, form an imidazole ring.

With reference to compounds of the formula (II) wherein A¹, B and C are in the second alternative, one preferred class of compounds has A¹ and B taken together as 1,3-propylene, more preferably with C as methyl and W¹ as hydrogen. Most preferred compounds in this subclass have W and Y¹ as hydrogen and X¹ as 3-methoxy; W as hydrogen, X¹ as hydrogen or 3-chloro and Y¹ as 4-methoxy; or W as 6-chloro and X¹ and Y¹ as hydrogen. A second preferred class have W, W¹ and Y¹ as hydrogen with X¹ as 3-chloro. Most preferred compounds in this subclass have A¹ and B as 1,3-propylene and C as benzyl or methyl; or A¹ and B as 1,4-butylene and C as methyl.

Finally, the present invention encompasses a method of treating anxiety in a hyperanxious person which comprises treating said person with an anxiolytic amount of a compound of the formula wherein
in a first alternative
A² is hydrogen or methyl, and
B¹ and C¹ are each independently hydrogen, $(C_1-C_2)$alkyl, phenyl or benzyl;
in a second alternative
A² is hydrogen or methyl, and
B¹ and C¹ together with the nitrogen atom to which they are attached, form a piperidine, pyrrolidine, morpholine or imidazole ring;
in a third alternative
A² and B¹ together are 1,3-propylene, 1,4-butylene or 1,5-pentylene, and C¹ is hydrogen, $(C_1-C_2)$alkyl, phenyl or benzyl;
W is hydrogen, $(C_1-C_2)$alkyl, $(C_1-C_2)$alkoxy, chloro or fluoro; and
$W^1$, $X^1$ and $Y^1$ are each independently hydrogen, $(C_1-C_2)$alkyl, $(C_1-C_2)$alkoxy, $(C_1-C_2)$alkylthio, bromo, chloro, fluoro, trifluoromethyl, hydroxy, formyl, carboxamido, $(C_1-C_2)$alkylcarboxamido, di$(C_1-C_2)$alkylcarboxamido, cyano, nitro, amino, $(C_1-C_2)$alkylamino or di$(C_1-C_2)$alkylamino;

With the proviso that when A² is hydrogen or methyl, B¹ and C¹ are each independently hydrogen, $(C_1-C_2)$alkyl, phenyl or benzyl, and any one of W¹, X¹ and Y¹ is 4-chloro, at least one of W¹, X¹ and Y¹ is other than hydrogen.

It will be noted that when the compounds of the formula (III) are in the first alternative, most of the compounds of the formula (I) fall within the scope thereof. In said first alternative, a first group of compounds preferred for anxiolytic use have A², W, W¹, and Y¹ as hydrogen, and B¹ and C¹ as methyl. Most preferred compounds with this subclass have X¹ as 3-chloro, 3-methoxy, 3-fluoro, 3-methyl or 3-cyano. A second preferred group within this first alternative has A², W and W² as hydrogen, Y¹ as 4-methoxy and B¹ and C¹ as methyl; most preferably, X¹ as chloro or fluoro.

Compounds of the formula (III) in the second and third alternatives fully correspond to compounds of the formula (II) as defined above, so that preferred use of these compounds fully corresponds to preferred compounds as detailed above.

DETAILED DESCRIPTION OF THE INVENTION

Compounds of the present invention are readily prepared by a variety of Methods A to H, as detailed below.

Method A—Reaction of an Amide Dialkylacetal with a 1-Phenyl-2(1H,3H)-indolone

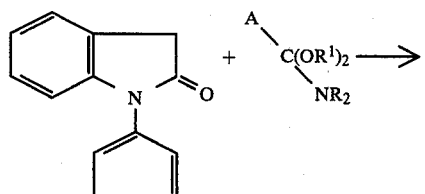

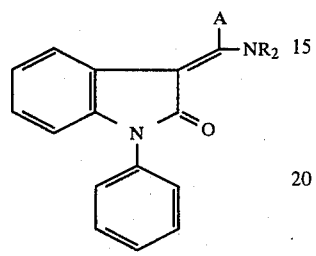

herein A and R are as previously defined (except that generally R will be other than hydrogen), $R^1$ is $(C_1-C_3)$alkyl, and aromatic rings are appropriately substituted according to the formulae (I), (II) and (III).

Because of the ready availability of the required amide dimethyl acetals, this is one of the preferred methods when R is methyl. The reaction is usually carried out in the presence of a reaction-inert solvent or diluent (i.e., a solvent which does not interact with starting materials, reagents or product to significantly depress yield of the desired product). Chloroform is the preferred solvent. Temperature is not critical, although it is usually elevated (50°–100° C.) to assure that reaction will occur at a reasonable rate. The reflux temperature of chloroform is particularly convenient, when the latter is used as solvent. At least one equivalent of the amide acetal is used, in order to maximize yield based on the indolone. Use of a slight excess of the acetal is helpful in assuring complete conversion of the indolone within a reasonable time. Product is generally isolated by evaporation, and is optionally purified by chromatography and/or crystallization.

The starting indolones required for syntheses according to Method A are generally available by cyclization of an appropriately substituted N-phenyl-alpha-haloacetanilide (Method J, below), in turn made by alpha-haloacetylation of the appropriately substituted diphenylamine (Method K, below); by basic hydrazine hydrate reduction of the corresponding isatin, in turn made from the appropriately substituted diphenylamine and oxalyl chloride (see Preparation M1 and M2 below); or halogenation/hydrolysis of appropriately substituted 1-arylindoles (Method L, below), in turn made by arylation of indole (Method C, below).

The aromatic halides required for these and other syntheses described below are available commercially or by literature methods, for example, m-iodoethylbenzene by diazotization/KI treatment of m-ethylaniline (Ann. 714:109, 1968); p-bromo-o-fluoroanisole by bromination of o-fluoroanisole (J. Prakt. Chem. 143: 18–28, 1935); o-chloro-p-iodoanisole by chlorination of p-iodoanisole (J. Chem. Soc. 1931:1121–1123); alkylation of appropriately substituted phenols (see Preparation E2 below). Required diphenylamines are likewise available commercially; by literature methods, e.g., di-(4-methoxyphenyl)amine by an improved Ullman procedure (J. Org. Chem. 26:2721, 1961); or by the arylation/hydrolysis of acetanilides (see Method C, Preparation C45, below).

Method B—Reaction of an Amide, Activated by POCl$_3$, with a 1-Phenyl-2(1H,3H)-indolone

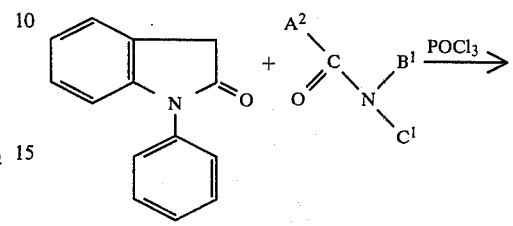

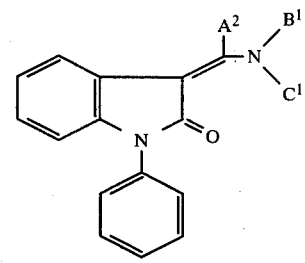

wherein $A^2$, $B^1$ and $C^1$ are as previously defined and aromatic rings are appropriately substituted according to the formulae (I), (II) and (III).

The procedure of Method B is essentially that used in Belgian Pat. No. 849,626 at pages 11–12 for the preparation of 1-phenyl-3-(dimethylaminomethylene)-2-(1H,3H)-indolone from the 1-phenylindolone and dimethylformamide. The amide, usually in the presence of a reaction-inert diluent (as defined above), such as toluene, is reacted with the phosphorous oxychloride at 0°–30° C. for a short period of time (10–30 minutes). There should generally be at least one mole of amide per mole of POCl$_3$; usually an excess (up to 2.5 moles) of the amide is used. The appropriately substituted 1-phenyl-2(1H,3H)-indolone (usually about 0.67 to 1 mole/mole of POCl$_3$) is added and the reaction warmed at 50°–100° C. until reaction is substantially complete. At 65°–70° C., a reaction time of 16–18 hours is generally suitable.

Alternatively, an iminoether is used as the activated form of an amide derived from NH$_3$ or a primary amine. The iminoether is reacted directly with the 1-phenyl-2(1H,3H)-indolone is a reaction-inert solvent, generally at elevated temperature (75°–125° C.); cf Example M1–M3 below. The iminoethers are prepared by standard methods, e.g., the well known reaction of triethyloxonium fluoroborate with the amide.

The amides required for the present syntheses are available commercially or by reaction of a secondary amine with acetate or formate ester, acetic or formic acid or an activated form thereof such as acetyl chloride, acetic anhydride or acetoformic acid reagent; or by cyclization of suitable omega-amino acids or their derivatives. The required 1-phenyl-2(1H,3H)-indolones are synthesized as described above.

Method C—Arylation of 3-Substituted(1H,3H)-Indolones

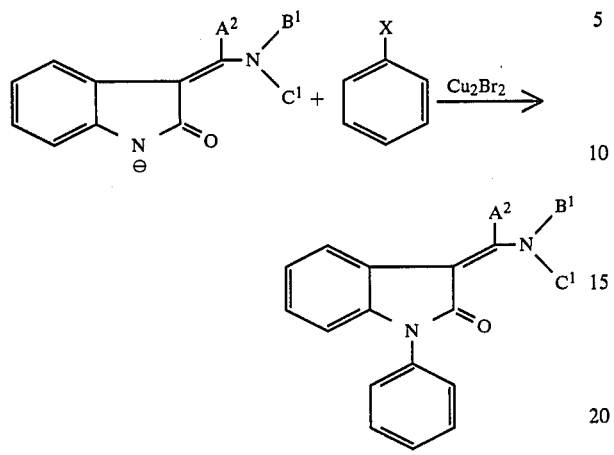

wherein $A^2$, $B^1$ and $C^1$ are as hereinbefore defined (except that generally both $B^1$ and $C^1$ are other than hydrogen), X is iodo or bromo, and aromatic rings are appropriately substituted according to the formulae (I), (II) and (III).

The first stage of the procedure of Method C is generally conversion of the starting indolone to its alkali metal salt, preferrably done with a molar equivalent or a reagent such as NaH, which forms the required salt irreversibly. Salt formation is preferrably carried out in a solvent, one which is reaction-inert, as defined above; dry dimethylformamide is well-suited for this purpose. Temperature is not critical but ambient temperatures (e.g., 15°-30° C.) are usually well-suited, avoiding the expense of heating or cooling. Salt formation is rapid and, with NaH as reagent, is judged complete when evolution of hydrogen ceases. The aromatic bromide or iodide (usually at least one molar equivalent, but optionally with up to 2 molar equivalents in excess to assure complete conversion of the starting indolone) and cuprous bromide ($Cu_2Br_2$, usually substantially one mole/mole of indolone) are added, and the reaction mixture heated to elevated temperatures (100°-200° C.) until the reaction is substantially complete. A reaction time of 40 hours at 135°-140° C. is typical. The product is readily isolated by quenching the reaction with ice and water, extracting the product into a water immisible solvent, and evaporation. If desired, the product is further purified by chromatography and/or recrystallization.

The starting indolones are available from simple 2(1H,3H)-indolones, suitably substituted on the aromatic ring, by reaction with amides or amide acetals according to Methods A and B. The availability of the starting halides is described above.

Method D—Dealkylation of a Preformed Compound Containing Aromatic ($C_1$-$C_2$)Alkoxy Compounds of the formula (III) containing an aromatic hydroxy group are preferably prepared by cleavage of the corresponding ($C_1$-$C_2$)alkoxy derivatives, most preferably from the corresponding methoxy derivative. A reagent particularly selective for this purpose is boron tribromide, used in excess (e.g., 3 moles/mole of substrate), in a reaction-inert solvent, e.g., methylene chloride. The reagents are usually combined at low temperature ($-50°$ to $-100°$ C., conveniently $-78°$ C., the temperature of a dry ice-acetone bath and then allowed to warm to ambient temperature (e.g., over 2 hours at 25° C.), then quenched into water with brief stirring (e.g., 15 minutes at 25° C.). Acidification, extraction into a water immiscible solvent and evaporation provides a convenient isolation of the product. If desired the product is further purified by chromatography and/or recrystallization.

Method E—Alkylation of a Preformed Compound Containing a Phenolic Group

Compounds of the formula (III) containing a ($C_1$-$C_2$)alkoxy group are alternatively prepared by reaction of an alkylating agent (e.g., ethyl iodide, dimethyl sulfate) with a preformed compound of the formula (III) containing a phenolic group. The phenol is generally alkylated with an excess of alkylating agent (assuring complete reaction in a reasonable time period) in a reaction-inert solvent, in the presence of an excess of an insoluble base such as $K_2CO_3$ which takes up the acid produced in the alkylation, at 50°-100° C.

Method F—Replacement of the Amino Function in an Aminoalkylidene Derivative with a Second Amino Function Compounds of the formula (III) wherein the group $-NB^1C^1$ is an amino group (open chain or cyclic) are conveniently prepared by replacement of a first amine group by reaction with the second amine present in four or more molar excess. The reaction is carried out in a reaction-inert solvent, such as ethanol, conveniently at ambient temperature (15°-30° C.) until the reaction is substantially complete (e.g., 16 hours at 25° C.) and products recovered by simple evaporation in vacuo, with optional purification by chromatography and/or recrystallization. This method is a preferred route for preparing compounds of the formulae (I), (II) or (III) containing a primary amino or cyclic secondary amino function. The preferred precursors are 3-(1-dimethylaminoalkylidene) derivatives, readily available according to Method A.

Method G—Replacement of the Hydroxy Function in a Hydroxyalkylidene Group with an Amine Function The preferred route to compounds of the formulae (I), (II) or (III) containing a imidazolealkylidene group is to react the corresponding hydroxyalkylidene derivative with carbonylidiimidazole (1-1.1 molar equivalents) in a reaction inert solvent such as benzene or toluene, conveniently at ambient temperature (15°-30° C.). Such products generally crystallize directly from the exemplified solvents (benzene or toluene), but are otherwise recovered by evaporation with optional purification by chromatography and/or recrystallization.

The required hydroxymethylene and 1-hydroxyethylidene starting materials are readily available by standard base catalyzed condensation of formate or acetate ester with the appropriately substituted 1-phenyl-2(1H,3H)-indolone.

Method H—Replacement of Alkoxy Function in an Alkoxyalkylidene Group with an Amino Function Compounds of the formula (II) wherein the group $-NB^1C^1$ is an amino group are also conveniently prepared by replacement of an ($C_1$-$C_2$)alkoxy function in a 1-phenyl-3-(1-alkoxyalkylidene)-2(1H,3H)-indolone, suitably substituted on aromatic rings, using conditions otherwise analogous to those of Method F.

The required 3-(1-alkoxyalkylidene) precursors are obtained by condensation of orthoformate or orthoacetate with the appropriate 1-phenyl-2(1H,3H)-indolone (see Preparation M5, below), in turn available by methods described above.

The clinical utility of the novel compounds of the present invention in the treatment of individuals suffering from schizophrenia is reflected by their potent gabaergic activity. Gabaergic activity refers to the gamma-aminobutyric acid like activity of these compounds in inhibiting convulsions induced by 3-mercaptopropionic acid in an animal model (see for example Roberts and Taberner, Brit. J. Pharmacol. 61:476P, 1977; Adcock and Taberner, Biochem. Pharmacol. 27:246; 1978). Subjects in the present test were Charles-River male mice, Swiss CD strain, 17–21 g., fasted for 18 hours prior to testing. Compounds were administered subcutaneously or orally in a vehicle consisting of 5% ethanol, 5% emulphor 620 and 90% saline, which vehicle alone served as a control treatment. Compounds were tested on a $0.5 \times \log_{10}$ dosage continuum, if active, to achieve data for determination of an $ED_{50}$ value. Solution concentrations were varied at different doses to provide a constant injection volume of 10 ml/kg. The grouped mice were treated with test compounds, and, 1 hour later with 3-mercaptopropionic acid (MPA), 32 mg/kg, intraperitoneally, after which they were observed continuously for 10 minutes. In untreated mice this MPA challange causes clonic convulsions within 4 minutes of treatment. Protection against MPA convulsions in a given mouse was said to occur if no convulsions occurred during the 10 minute test period. In this test, compounds of the formula (I) showed potent activity. For example, subcutaneous $ED_{50}$ values ranged from 6.6 mg/kg for 1-(3-fluoro-4-methoxyphenyl)-3-(dimethylaminomethylene)-2(1H,3H)-indolone to about 56 mg/kg for the otherwise corresponding 1-(4-methylpheny) and 1-(4-methylthiophenyl) analogs. 1-Phenyl-3-(dimethylaminomethylene)-2(1H,3H)-indolone and an extensive number of analogous compounds showed no activity in this test, even at 100 mg/kg. Only a very few compounds of the formula (II) demonstrate such activity, e.g., 1-(3-fluoro-4-methoxyphenyl)-3-(2-pyrrolidinylidene)-2(1H,3H)-indolone; the N-methyl analog thereof; and, in particular, 1-(4-methoxyphenyl)-3-(1-methyl-2-pyrrolidinylidene)-2(1H,3H)-indolone which shows an $ED_{50}$ of 3.2–5.6 mg/kg subcutaneously and 18–32 mg/kg orally.

The clinical utility of novel and known compounds of the present invention [formulae (II) and (III)] in the treatment of hyperanxiety is reflected in their potent in vivo effect on 3H-flunitrazepam (3H-FNP) binding. This effect was measured by the method of Koe and Weissman, J. Clin. Pharmacol. 21:397S, 1981. Groups of five mice, of the type described above, are injected subcutaneously with 320 micromole/kg of the test compound or vehicle 1 hour prior to an intravenous injection of 200 microCi/kg $^3$H-FNP. Twenty minutes after the $^3$H-FNP injection, the mice were sacrificed by cervical dislocation, and the brains were removed and immediately frozen. Each brain was weighed quickly and homogenized in 40 volumes (w/v) ice-cold 50 mM Tris HCl pH 7.7 buffer using a Brinkmann Polytron. Triplicate 1.0-ml samples were filtered through Whatman GF/B glass fiber filters under vacuum and washed with two 5 ml aliquots of the ice-cold buffer. The bound $^3$H-FNP was measured by adding the filters to vials containing 10 ml. Aquasol-2 and counting the radioactivity. Bound $^3$H-FNP for drug-treated mice was calculated as percentage of bound $^3$H-FNP for vehicle-treated mice. In this test, compounds of the formula (II) or (III) exhibit enhancement in $^3$H-FNP binding, for example, ranging from 126% for 1-(3-chlorophenyl)-3-(morpholinomethylene)-2(1H,3H)-indolone and 1-(3-cyanophenyl)-3-(1-methyl-2-pyrrolidinylidene)-2(1H,3H)-indolone to greater than 250% for the most highly active compounds such as 1-(3-chloro-4-methoxyphenyl)-3-(dimethylaminomethylene)-2(1H,3H)-indolone and 1-(3-fluoro-4-methoxy)-3-(1-methyl-2-pyrrolidinylidene)-2(1H,3H)-indolone.

In the treatment of a person suffering from schizophrenia (alleviating schizophrenia per se, or reversing or inhibiting the tardive dyskinesia side effects of an earlier or concurrently administered neuroleptic agent) or in the treatment of a person suffering from hyperanxiety, the compounds of the present invention are administered by a variety of conventional routes of administration including orally and parenterally. Preferably, the compounds are administered orally, generally in single or multiple daily doses of about 0.02 to 12 mg/kg body weight of the subject to be treated, preferably about 0.05 to 5 mg/kg. If parenteral administration is desired, then these compounds are given in single or multiple daily doses of 0.01 to 6 mg/kg body weight of the subject to be treated. However, at the discretion of the attending physician, there can be some variation in dosage outside of the specified ranges, depending upon the condition of the subject being treated and the particular compound employed.

The compound is administered alone or in combination with pharmaceutically-acceptable carriers or diluents, in either single or multiple doses. Suitable pharmaceutical carriers include inert diluents or fillers, sterile aqueous solutions and various organic solvents. The pharmaceutical compositions formed by combining the novel compounds of formula I or salts thereof and pharmaceutically acceptable carriers are readily administered in a variety of dosage forms such as tablets, powders, capsules, lozenges, syrups and the like. These pharmaceutical compositions can, if desired, contain additional ingredients such as flavorings, binders, excipients and the like. Thus, for oral administration, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols. When aqueous suspensions or elixirs are desired for oral administration, the essential active ingredient therein may be combined with various sweetening or flavoring agents, coloring matters or dyes and, if desired, emulsifying agents or suspending agents, together with diluents such as water, ethanol, propylene glycol, glycerin, or combinations thereof.

Preferably, the products of this invention are administered orally in unit dosage form i.e., as a single physically discrete dosage unit containing an appropriate amount of the active compound in combination with a pharmaceutically-acceptable carrier or diluent. Examples of such unit dosage forms are tablets or capsules containing from about 1 to 500 mg of the active ingredient, a compound of formulae (I), (II) or (III) comprising from about 10% to 90% of the total weight of the dosage unit.

For parenteral administration, solutions or suspensions of the compounds of formulae (I), (II) or (III) in sterile aqueous solutions, for example aqueous propylene glycol, sodium chloride, dextrose or sodium bicarbonate solutions are employed. Such dosage forms are suitably buffered, if desired. The preparation of suitable sterile liquid media for parenteral administration will be well known to those skilled in the art.

It has been noted that at least one of the compounds of the present invention, viz., 1-(4-methoxyphenyl)-3-(1-methyl-2-pyrrolidinylidene)-2(1H,3H)-indolone, also possesses valuable antidepressant activity, as shown by testing in the antidepressant animal model of Porsolt et al., European J. Pharmacol. 47, pp. 379-391 (1978). It is further noted that the compounds of the present invention possessing the above gabaergic activity are also valuable in the treatment of epilepsy, i.e., in preventing the epileptic seizures associated with that disease. In the treatment of depression, or in the treatment of epilepsy, compounds of the present invention having said antidepressant, or gabaergic activity, respectively, are formulated and administered clinically in the same manner and range of dosage as that disclosed above for the treatment of schizophrenia or hyperanxiety. Based on their excellent gabaergic activity, as well as ease of preparation, preferred compounds for the treatment of epilepsy correspond to those preferred in the treatment of schizophrenia.

The present invention is illustrated by the following examples. However, it should be understood that the invention is not limited to the specific details of these examples. All temperatures are in degrees centigrade.

METHOD A

EXAMPLE A1

1-(3-Chloro-4-methoxyphenyl)-3-(1-dimethylaminoethylidene)-2(1H,3H)-indolone 1-(3-Chloro-4-methoxyphenyl)-2(1H,3H)-indolone (0.67 g, 2.45 mmole), dimethylacetamide dimethylacetal (90%, 0.45 ml, 2.7 mmole) and 10 ml CHCl$_3$ were refluxed under nitrogen for 3 hours. The reaction mixture was cooled and evaporated in vacuo to a viscous oil. The oil was column chromatographed on silica gel, eluting impurities with ethyl acetate and then product with 2-4% methanol in ethyl acetate, initially isolated as an oil (793 mg). Crystallization from ether gave purified title product, 625 mg, m.p. 138°-141°.

Anal. Calcd. for C$_{19}$H$_{19}$N$_2$O$_2$Cl: C, 66.56; H, 5.59; N, 8.17; m/e 344/342

Found: C, 66.43; H, 5.34; N, 8.14; m/e 344/342

EXAMPLE A2

1-Phenyl-3-(1-dimethylaminoethylidene)-6-chloro-2(1H,3H)-indolone and 1-(3-chlorophenyl)-3-(1-dimethylaminoethylidene-2(1H,3H)-indolone By the procedure of Example A1, a mixture of 1-(3-chlorophenyl)-2(1H,3H)-indolone and 1-phenyl-6-chloro-2(1H,3H)-indolone (5.0 g, 0.21 moles) was converted to a crude mixture of title products as an oil. Chromatography on silica gel, using ethyl acetate, separated and purified the title isomers. The less polar, faster moving product, was the 3-chlorophenyl isomer, crystallized from ether, 904 mg, m.p. 113°-116°.

Anal. Calcd. for C$_{18}$H$_{17}$N$_2$OCl: C, 69.11; H, 5.48; N, 8.96; m/e 314/312

Found: C, 69.20; H, 5.52; N, 9.08; m/e 314/312

The more polar, slower eluting product was the 6-chloro isomer, an oil which crystallized on standing and which was triturated with pentane, 0.305 g, m.p. 118°-121°.

Anal. Calcd. for C$_{18}$H$_{17}$N$_2$OCl: C, 69.11; H, 5.48; N, 8.96; m/e 314/312

Found: C, 68.97; H, 5.47; N, 8.08; m/e 314/312

EXAMPLE A3

1-(3-Chlorophenyl)-3-(dimethylaminomethylene)-2(1H,3H)-indolone

By the procedure of Example A1, but substituting an equivalent of dimethylformamide dimethylacetal for the dimethylacetamide dimethylacetal, using first methylene chloride and then 7.5% ethyl acetate in methylene chloride in chromatography and recrystallization from ether-pentane, 1-(3-chlorophenyl)-2(1H,3H)-indolone (10 g, 0.041 mole) was converted to title product, 3.73 g, m.p. 116°-118°.

Anal. Calcd. for C$_{17}$H$_{15}$N$_2$OCl: C, 68.34; H, 5.06; N, 9.38

Found: C, 67.99; H, 4.82; N, 9.25

EXAMPLE A4

1-(3-Fluorophenyl)-3-(dimethylaminomethylene)-2(1H,3H)-indolone

By the procedure of Example A1, but using 13:7 hexane:ethyl acetate and then 3:7 hexane:ethyl acetate as eluant and ether/pentane for crystallization, 1-(3-fluorophenyl)-2(1H,3H)-indolone (0.80 g, 3.5 mmoles) was converted to title product, 0.53 g, m.p. 87°-88.5°.

Anal. Calcd. for C$_{17}$H$_{15}$N$_2$OF.0.1H$_2$O: C, 71.86; H, 5.39; N, 9.86; m/e 282

Found: C, 71.57; H, 5.10; N, 9.84; m/e 282

EXAMPLE A5

1-(4-Methoxyphenyl)-3-(1-methyl-2-pyrrolidinylidene)-2(1H,3)-indolone 1-(4-Methoxyphenyl)-2(1H,3H)-indolone (49 g, 0.205 mole), N-methyl-2-pyrrolidone dimethyl acetal (ca. 80%, 53 g, 0.245 mole, Ber, 97, pp. 3081-7, 1964) and 1000 ml chloroform were refluxed under nitrogen for 1.5 hours. The reaction mixture was cooled and evaporated in vacuo to solids. Two recrystallizations from ethyl acetate gave purified title product, 44.7 g, m.p. 90°-93° C. Thirty grams of this material were dried at 80° C./15 mm Hg for 20 hours to give 26.1 g of title product, m.p. 127°-9° C.

Anal. Calcd. for C$_{20}$H$_{20}$N$_2$O$_2$: C, 74.97; H, 6.29; N, 8.75; m/e 320

Found: C, 74.99; H, 6.29; N, 8.59; m/e 320

EXAMPLES A6-A10

Method A (Examples A1-A5) was further employed to prepare the following additional compounds. Listed in sequence are: example number; name of product; name of starting materials; chromatography eluant;

crystallization solvent(s); yield; m.p.; C, H and N microanalysis (calculated) found.

A6. 5-Fluoro-1-(4-fluorophenyl)-3-(dimethylaminomethylene)-2(1H,3H)-indolone; 5-fluoro-1-(4-fluorophenyl)-2(1H,3)-indolone/dimethylformamide dimethylacetal; no chromatography; ether/CH$_2$Cl$_2$; 63%; 149-151; (66.98) 66.76, (4.80) 4.50, (9.19) 9.12 for 0.25 H$_2$O.

A7. 6-Fluoro-1-phenyl-3-(dimethylaminomethylene)-2(1H,3H)-indolone; 6-fluoro-1-phenyl-2(1H,3H)-indolone/dimethylformamide dimethylacetal; no chromatography; ethyl acetate/hexane; 76%; 155°-157.5°; (71.18) 71.10, (5.45) 5.49, (9.77) 10.12 for 0.25 H$_2$O.

A8. 6-Chloro-1-phenyl-3-(dimethylaminomethylene)-2(1H,3)-indolone; 6-chloro-1-phenyl-2(1H,3)-indolone/dimethylformamide dimethylacetal; ethyl acetate/hexane; benzene/pentane; 18%; 148°-151°; (68.34) 68.69, (5.06) 5.22, (9.38) 9.71.

A9. 1-(3-Fluoro-4-methoxyphenyl)-3-(1-dimethylaminoethylidene)-2(1H,3H)-indolone; 1-(3-fluoro-4-methoxyphenyl)-2(1H,3H)-indolone/dimethylacetamide dimethylacetal; ethyl acetate; ether; 48%; 187°-189°; (69.92) 69.73, (5.87) 6.06, (8.59) 8.40.

A10. 1-(4-Methoxyphenyl)-3-(1-dimethylaminoethylidene-2(1H,3H)-indolone; 1-(4-methoxyphenyl)-2(1H,3H)-indolone/dimethylacetamide dimethylacetal; ethyl acetate; ether; 66%; 176°-177.5°; (74.00) 73.81, (6.54) 6.43; (9.09) 8.79.

PREPARATION A11

3-(Dimethylaminomethylene)-2(1H,3H)-indolone 2-(1H,3H)-indolone (oxindole, 50 g, 0.376 mole), dimethylformamide dimethylacetal (50 ml, 0.376 mole) and CHCl$_3$ (300 ml) were combined and refluxed for 6 hours. The reaction mixture was concentrated in vacuo to 150 ml and title product recovered by filtration, 59.5 g, m.p. 192°-197°. A second crop was obtained from mother liquor, 6.9 g, m.p. 193°-196°. See Ber. 85:744-779 (1952) and Chem. Pharm. Bull. 23:1436-1439 (1975).

Additional preparations by Method A (no chromatography or recrystallization):

A12. 3-[1-(Dimethylamino)ethylidene]-2(1H,3H)-indolone; oxindole/dimethylacetamide dimethylacetal; 87%; 204°-207°.

A13. 4-Chloro-3-(dimethylaminomethylene)-2(1H,3H)-indolone; 4-chlorooxindole/dimethylformamide dimethylacetal; 82%; 220°-223°.

A14. 6-Chloro-3-(dimethylaminomethylene)-2(1H,3H)-indolone; 6-chlorooxindole/dimethylformamide dimethylacetal; 100%; 224°-226°.

A15. 7-Chloro-3-(dimethylaminomethylene)-2(1H,3H)-indolone; 7-chlorooxindole/dimethylformamide dimethylacetal; 70%; 230°-232°.

A16. 5-Methoxy-3-(dimethylaminomethylene-2(1H,3H)-indolone; 5-methoxyoxindole/dimethylformamide dimethylacetal; 66%; 222°-225°.

A17. 5-Chloro-3-(dimethylaminomethylene)-2(1H,3H)-indolone; 5-chlorooxindole/dimethylformamide dimethylacetal; 67%; 204°-206°.

METHOD B

EXAMPLE B1

1-(3-Chlorophenyl)-3-(1-benzyl-2-pyrrolidinylidene)-2(1H,3H)-indolone

N-benzyl-2-pyrrolidone (1.58 ml, 9.85 mmoles) was combined with 2 ml toluene under N$_2$ and cooled to 0°-5°. POCl$_3$ (0.5 ml, 5.9 mmoles) was added and the mixture stirred 30 minutes. Toluene (3 ml) and 1-(3-chlorophenyl-2(1H,3H)-indolone (1.2 g, 4.92 mmoles) were added and the stirred reaction mixture warmed to 25° for 30 minutes and then to 70°-75° for 18 hours. The reaction mixture was cooled, diluted with 100 ml CH$_2$Cl$_2$, washed with saturated NaHCO$_3$, H$_2$O and brine, dried and concentrated in vacuo to an oil (2.6 g). The oil was chromatographed on silica gel (45×150 mm) using CH$_2$Cl$_2$ as eluant, yielding title product, initially an oil which was crystallized from ether/pentane, 1.04 g (53%), m.p. 72°-75°.

Anal. Calcd. for C$_{25}$H$_{21}$N$_2$OCl: C, 74.89; H, 5.28; N, 6.99; m/e 402/400

Found: C, 74.75; H, 5.41; N, 6.94; m/e 402/400

EXAMPLE B2

1-(3-Chlorophenyl)-3-(1-methyl-2-piperidylidene)-2(1H,3H)-indolone

By the procedure of Example B1, but using 1:1 hexane:ethyl acetate as chromatography eluant and pentane for crystallization, 1-(3-chlorophenyl-2-(1H,3H)-indolone (2.0 g, 8.2 mmoles) and N-methyl-2-piperidone (1.3 ml, 11.5 mmoles) were converted to title product, 180 mg (6.5%) m.p. 162°-165°.

Anal. Calcd. for C$_{20}$H$_{19}$N$_2$OCl: C, 70.90; H, 5.65; N, 8.27; m/e 340/338

Found: C, 70.79; H, 5.73; N, 8.05; m/e 340/338

EXAMPLE B3

1-(3-Chlorophenyl)-3-(1-methyl-2-pyrrolidinylidene)-2(1H,3H)-indolone and

6-Chloro-1-phenyl-3-(1-methyl-2-pyrrolidinylidene)-2(1H,3H)-indolone

By the procedure of Example B1 a mixture of 1-(3-chlorophenyl)-2(1H,3H)-indolone and 6-chloro-1-phenyl-2(1H,3H)-indolone (1.36 g, 5.56 mmoles) and N-methyl-2-pyrrolidone (0.9 ml, 9.34 mmoles) were converted to a crude mixture of title products, as an oil. The isomers were separated, purified and isolated as solid products by silica gel chromatography, using the same eluant. The 3-chlorophenyl isomer was the faster moving, yield 0.72 g, m.p. 134°-137°.

Anal. Calcd. for C$_{19}$H$_{17}$N$_2$OCl: C, 70.25; H, 5.28; N, 8.63; m/e 326/324

Found: C, 70.03; H, 5.26; N, 8.69; m/e 326/324

The more polar component was the 6-chloro isomer, yield 0.10 g, m.p. 177°-179°.

Anal. Calcd. for C$_{19}$H$_{17}$N$_2$OCl: C, 70.25; H, 5.28; N, 8.63; m/e 326/324

Found: C, 70.44; H, 5.30; N, 8.26; m/e 326/324

EXAMPLE B4

1-(3-Chloro-4-methoxyphenyl)-3-(1-methyl-2-pyrrolidinylidene)-2(1H,3)-indolone

By the procedure of Example B1, except that ethyl acetate was used as eluant and ether to crystallize the product, 1-(3-chloro-4-methoxyphenyl)-2(1H,3H)-indolone (1.05 g, 3.84 mole) and N-methyl-2-pyrrolidone (0.62 ml, 6.42 mmoles) were converted to title product, 0.58 g, m.p. 126°-127.5°.

Anal. Calcd. for C$_{20}$H$_{19}$N$_2$O$_2$Cl: C, 67.69; H, 5.40; N, 7.90; m/e 356/354

Found: C, 67.47; H, 5.47; N, 7.90; m/e 356/354

EXAMPLE B5

1-(3-Fluoro-4-methoxyphenyl)-3-(1-methyl-2-pyrrolidinylidene)-2(1H,3H)-indolone

By the procedure of Example B5, except to use ethyl acetate as eluant, 1-(3-fluoro-4-methoxyphenyl)-2(1H,3H)-indolone (2.0 g, 7.8 mmoles) and 1-methyl-2-pyrrolidone (1.5 ml, 15.6 mmole) were converted to title product, 0.32 g, m.p. 68°–71°.

Anal. Calcd. for $C_{20}H_{19}N_2O_2F$: C, 70.99; H, 5.66; N, 8.28; m/e 338

Found: C, 70.86; H, 5.85; N, 8.13; m/e 338

EXAMPLES B6–B9

Method B (Examples B1–B5) was further employed to prepare the following additional compounds. Listed in sequence are example number; name of product; starting materials; chromatography eluant; crystallization solvent(s); yield; m.p.; C, H and N microanalyses (calculated) found.

B6. 1-(Chlorophenyl)-3-(N-phenyl-N-methylaminomethylene)-2(1H,3H)-indolone; 1-(3-chlorophenyl-2(1,3H)-indolone/N-phenyl-N-methylformamide; 1:1 hexane:ethyl acetate; ether/pentane; 19%; 127°–129°; (73.22) 73.26, (4.75) 4.84, (7.77) 7.77.

B7. 1-(3-Chlorophenyl)-3-(N-ethyl-2-pyrrolidinylidene)-2(1H,3H)-indolone; 1-(3-chlorophenyl)-2(1H,3)-indolone/N-ethyl-2-pyrrolidone; chloroform; ethyl acetate/hexane; 38%; 105°–107°; (70.90) 70.96, (5.65) 5.84, (8.27) 8.46.

B8. 1-(3-Chlorophenyl)-3-(N-phenyl-2-pyrrolidinylidene)-2(1H,3)-indolone; 1-(3-chlorophenyl)-2(1H,3H)indolone/N-phenyl-2-pyrrolidone; 1:1 ethyl acetate:hexane; ether; 33%; 128°–130°; (74.51) 74.53, (4.95) 5.04, (7.24) 7.22.

B9. 4-Chloro-1-phenyl-3-(N-methyl-2-pyrrolidinylidene)-2(1H,3H)-indolone; 4-chloro-1-phenyl-2(1H,3H)-indolone/N-methyl-2-pyrrolidone; ethyl acetate; ether/hexane; 20%; 78°–80°; (70.25) 69.89, (5.28) 5.56, (8.63) 8.52.

PREPARATION B10

3-(1-methyl-2-pyrrolidinylidene)-2(1H,3H)-indolone

Under nitrogen, N-methyl-2-pyrrolidone (3 ml) was cooled in an ice-water bath. Phosphorus oxychloride (0.91 ml, 0.01 mole) was added dropwise. After stirring 15 minutes, the bath was removed and 2(1H,3H)-indolone (oxindole, 1.3 g, 0.01 mole) in 3 ml. additional N-methyl-2-pyrrolidone (3 ml) was added dropwise. The temperature rose to 40° C. The reaction mixture was then heated at 80° for 16 hours, cooled and partitioned between ethyl acetate and water. The aqueous layer was washed with fresh ethyl acetate, basified to pH 9 with 6N NaOH and clarified by filtration. The filtrate was extracted with ethyl acetate. The extract was evaporated to dryness and the resulting title product triturated with ethyl acetate, 0.24 g, m.p. 268°–271° C. (dec). See Ind. J. Chem. 12:940–942 (1974).

Additional preparations by Method B:

B11. 6-Chloro-3-(1-methyl-2-pyrrolidinylidene)-2-(1H,3H)-indolone; 6-chlorooxindole/1-methyl-2-pyrrolidone; no chromatography; no recrystallization; 50%; 227°–229°.

B12. 3-[1-(p-chlorobenzyl)-2-pyrrolidinylidene]-2-(1H,3H)-indolone; oxindole/1-(p-chlorobenzyl)-2-pyrrolidone; no chromatography; methanol/ethyl acetate; 46%; 188°–190°.

METHOD C

EXAMPLE C1

1-(3-Methoxyphenyl)-3-(dimethylaminomethylene)-2(1H,3H)-indolone

In a flame dried flask under nitrogen, sodium hydride (50% dispersion in oil, 0.96 g, 20 mmoles) was washed free of oil with hexane. Dry dimethylformamide (DMF, 50 ml) and 3-(dimethylaminomethylene)-2(1H,3H)-indolone [Chem. Ber. 85:774 (1952); 3.77 g, 20 mmoles] were added, and the mixture stirred for 30 minutes (until gas evolution ceased). m-Indoanisole (9.36 g, 40 mmoles) in 20 ml DMF was added, followed by $Cu_2Br_2$ (5.74 g, 20 mmoles). The reaction mixture was heated at 120°–130° for 40 hours, poured over 300 g of ice, stirred with 300 ml ether, filtered and the ether layer separated, dried over $MgSO_4$, filtered and concentrated to an oil. The oil was chromatographed on silica gel, using ethyl acetate as eluant and title product initially isolated as an oil, crystallized from ether, 2.46 g (42%), m.p. 106°–108.5° (dec.).

Anal. Calcd. for $C_{18}H_{18}N_2O_2$: C, 73.45; H, 6.16; N, 9.52; m/e 294

Found: C, 73.83; H, 5.95; N, 9.49; m/e 294

EXAMPLE C2

1-(3-Fluoro-4-methoxyphenyl)-3-(dimethylaminomethylene)-2(1H,3)-indolone

By the procedure of Example C1, without chromatograpy, but directly crystallizing the crude product from ether/pentane, 3-(dimethylaminomethylene)-2-(1H,3H)-indolone (3.77 g, 20 mmoles) and 4-bromo-2-fluoroanisole (4.10 g, 20 mmoles) with NaH (0.96 g of 50% dispersion in oil, 20 mmoles) and $Cu_2Br_2$ (5.74 g, 20 mmoles), were converted to title product, 0.79 g, m.p. 113°–114°.

Anal. Calcd. for $C_{18}H_{17}N_2O_2F$: C, 69.21; H, 5.49; N, 8.97; m/e 312

Found: C, 69.06; H, 5.55; N, 8.95; m/e 312

EXAMPLE C3

1-(3-Trifluoromethylphenyl)-3-(dimethylaminomethylene)-2(1H,3H)-indolone

Using the same reagent quantities and the procedure of Example C2, but replacing the anisole with m-trifluoromethylphenyl bromide (7.9 ml, 50 mmoles), title product was prepared, 1.43 g, m.p. 103°–106°.

Anal. Calcd. for $C_{18}H_{15}N_2OF_3$: C, 65.05; H, 4.55; N, 8.43; m/e 332.

Found: C, 64.97; H, 4.53; N, 8.65; m/e 332.

EXAMPLE C4

1-(3-Methylphenyl)-3-(dimethylaminomethylene)-2(1H,3H)-indolone

Using the same reagent quantities and the procedure of Example C1, but replacing the iodoanisole with m-iodotoluene (5.1 ml, 40 mmoles), title product was prepared. Crystallization was from ether/pentane, 2.1 g, m.p. 105°–108°.

Anal. Calcd. for $C_{18}H_{18}N_2O$: C, 77.67; H, 6.52; N, 10.07; m/e 278

Found: C, 77.38; H, 6.46; N, 10.06; m/e 278

EXAMPLE C5

1-(3-Cyanophenyl)-3-(dimethylaminomethylene)-2(1H,3H)-indolone

Using the reagent quantities of Example C1, substituting 3-bromobenzonitrile (7.3 g, 40 mmoles) for the m-iodoanisole, 1:1 hexane:ethyl acetate as eluant in chromatography, and allowing the product to crystallize on standing, title product was otherwise prepared according to the procedure of Example C1, 1.3 g; m.p. 140°–143°.

Anal. Calcd. for $C_{18}H_{15}N_3O$: C, 74.72; H, 5.23; N, 14.52; m/e 289

Found: C, 74.32; H, 5.30; N, 14.43; m/e 289

EXAMPLE C6

1-(3-Methylphenyl)-3-(1-dimethylaminoethylidene)-2(1H,3H)-indolone

Using a reaction time of 18 hours at reflux and crystallizing the product from hexane after chromatography, 3-(1-dimethylaminoethylidene)-2(1H,3H)-indolone (4.06 g, 20 mmoles) was converted to present title product, 0.45 g, m.p. 96°–99°.

Anal. Calcd. for $C_{19}H_{20}N_2O$: C, 78.05; H, 6.90; N, 9.58; O, 5.47; m/e 292

Found: C, 77.85; H, 6.89; N, 9.57; O, 5.69; m/e 292

EXAMPLE C7

1-(3-Methoxyphenyl)-3-(1-methyl-2-pyrrolidinylidene)-2(1H,3H)-indolone

Under $N_2$, 3-(1-methyl-2-pyrrolidinylidene)-2(1H,3H)-indolone (1.0 g, 5 mmoles) was added portionwise to a slurry of NaH (50% oil dispersion, 265 mg., 5.5 mmoles) slurried in 50 ml. dimethylformamide and the mixture stirred at 25° for 2 hours. $Cu_2Br_2$ (1.43 g, 5 mmoles) and then m-bromoanisole (1.9 ml, 15 mmole) were added. The mixture was heated at 130° for 3.5 days, cooled, poured over ice and ethyl acetate, basified with $NH_4OH$ and filtered over a pad of diatomaceous earth. The aqueous layer was separated from the filtrate and extracted with fresh ethyl acetate. The combined organic layers were back-washed with $H_2O$, dried over $MgSO_4$, treated with activated carbon, evaporated to dryness and the residue triturated with ether, and filtered to yield starting material (110 mg). The ether filtrate was evaporated to an oil and chromatographed on 75 ml. silica gel, eluting with $CHCl_3$. Clean product fractions were combined, evaporated to an oil and crystallized from $CHCl_3$/ether, 320 mg, m.p. 127°–129° (dec).

Anal. Calcd. for $C_{20}H_{20}O_2N_2$: C, 74.98; H, 6.29; N, 8.74; m/e 320

Found: C, 74.87; H, 6.28; N, 8.69; m/e 320

EXAMPLES C8–C42

Method C (Examples C1–C7) was further employed to prepare the following additional compounds. Listed in sequence are: example number; name of product; name of starting materials; chromatography eluant; crystallization solvent(s); yield; m.p.; C, H and N microanalyses (calculated) found.

C8. 1-(3-Chloro-4-methoxyphenyl)-3-(dimethylamino-methylene)-2(1H,3H)indolone; 3-(dimethylaminomethylene)-2(1H,3H)-indolone/2-chloro-4-iodoanisole; ethyl acetate/hexane; benzene/pentane; 38%; 148°–151°; (65.75) 66.15, (5.21) 5.26, (8.52) 8.47.

C9. 1-(3-Ethylphenyl)-3-(dimethylaminomethylene)-2(1H,3H)-indolone; 3-(dimethylaminomethylene)-2(1H,3)-indolone/3-ethylphenyl iodide; ethyl acetate; ether/pentane; 34%; 112°–114°; (78.05) 77.75, (6.90) 6.88, (9.58) 9.53.

C10. 1-(3-Chloro-4-methoxy-5-methylphenyl)-3-(dimethylaminomethylene)-2(1H,3H)-indolone; 3-(dimethylaminomethylene)-2(1H,3H)indolone/2-chloro-4-bromo-6-methylanisole; 1:1 ethyl acetate:hexane; ether/pentane; 33%; 147°–150°; (66.56) 66.48, (5.59) 5.48, (8.17) 7.91.

C11. 1-(2-Methylphenyl)-3-(dimethylaminomethylene)-2(1H,3H)-indolone; 3-(dimethylaminomethylene)-2(1H,3H)-indolone/2-iodotoluene; ethyl acetate; hexane, then ether; 10%; 105°–107°; (77.67) 77.23, (6.52) 6.44, (10.07) 10.06.

C12. 1-(4-Methoxyphenyl)-3-(dimethylaminomethylene)-2(1H,3H)-indolone; 3-(dimethylaminomethylene)-2(1H,3H)-indolone/4-bromoanisole; not chromatographed; ether/pentane; 20%; 136°–138°; (73.45) 73.49, (6.16) 6.20, (9.52) 9.69.

C13. 1-(2-Chloro-5-trifluoromethylphenyl)-3-(dimethylaminomethylene)-2(1H,3H)-indolone; 3-(dimethylaminomethylene)-2(1H,3H)-indolone/2-chloro-5-trifluoromethylphenyl iodide; 1:1 ethyl acetate:hexane; ethyl acetate/hexane; 14%; 165°–167°; (58.94) 58.91, (3.85) 3.94, (7.64) 7.57.

C14. 1-(3,5-Dichlorophenyl)-3-(dimethylaminomethylene)-2(1H,3H)-indolone; 3-(dimethylaminomethylene)-2(1H,3H)-indolone/3,5-dichlorophenyl iodide; ethyl acetate; not recrystallized; 72%; 147°–149.5°; (61.27) 61.02, (4.23) 4.15, (8.41) 8.57.

C15. 5-Chloro-1-(3-chlorophenyl)-3-(dimethylaminomethylene)-2(1H,3H)-indolone; 5-chloro-3-(dimethylaminomethylene)-2(1H,3H)-indolone/3-chlorophenyl bromide; chloroform; not recrystallized; 24%; 165°–168°; (61.28) 61.34, (4.24) 4.26, (8.40) 8.32.

C16. 1-(2-Nitrophenyl)-3-(dimethylaminomethylene)-2-(1H,3H)-indolone; 3-(dimethylaminomethylene)-2(1H,3H)-indolone/p-bromonitrobenzene; not chromatographed; ether; 29%; 213°–215°; (66.01) 66.04, (4.89) 4.91, (13.59) 13.63.

C17. 1-(3-Bromophenyl)-3-(dimethylaminomethylene)-2-(1H,3H)-indolone; 3-(dimethylaminomethylene)-2(1H,3H)-indolone/m-dibromobenzene; not chromatographed; ether; 24%; 118°–121°; (59.49) 59.56, (4.41) 4.16, (8.16) 8.06.

C18. 1-(2-Chlorophenyl)-3-(dimethylaminomethylene)-2(1H,3H)-indolone; 3-(dimethylaminomethylene)-2(1H,3H)-indolone/o-chloroiodobenzene; no chromatography; ether/pentane; 12%; 169°–171°; (68.34) 67.95, (5.06) 5.30, (9.38) 9.45.

C19. 1-(2,5-Dichlorophenyl)-3-(dimethylaminomethylene)-2(1H,3H)-indolone; 3-(dimethylaminomethylene)-2(1H,3H)-indolone/2,5-dichloroiodobenzene; ethyl acetate; ether; 19%; 161°–163°; (61.27) 61.13, (4.23) 4.28, (8.41) 8.40.

C20. 1-(3,4-Dichlorophenyl)-3-(dimethylaminomethylene)-2(1H,3H)-indolone; 3-(dimethylaminomethylene)-2(1H,3H)-indolone/3,4-dichloroiodobenzene; not chromatographed; ether; 28%; 149°–151°; (61.27) 61.10, (4.23) 4.21, (8.41) 8.33.

C21. 1-(3-Nitrophenyl)-3-(dimethylaminomethylene)-2(1H,3H)-indolone; 3-(dimethylaminomethylene)-2(1H,3H)-indolone/m-iodonitrobenzene; not chromatographed; ethyl acetate/hexane; 51%; 113°–116°; (66.01) 65.90, (4.89) 4.92, (13.59) 13.53.

C22. 1-(4-Nitrophenyl)-3-(dimethylaminomethylene)-2(1H,3H)-indolone; 3-(dimethylaminomethylene)-2(1H,3H)-indolone/p-bromonitrobenzene; not chromatographed; ethyl acetate/hexane; 6%; 189°-192°; (64.14) 63.84, (5.07) 4.88, (13.20) 13.18 with 0.5 $H_2O$.

C23. 1-(3-Formylphenyl)-3-(dimethylaminomethylene)-2(1H,3H)-indolone; 3-(dimethylaminomethylene)-2(1H,3H)-indolone/3-iodobenzaldehyde; ethyl acetate; ether; 18%; 120°-122°; (73.95) 73.76, (5.52) 5.66, (9.59) 9.89.

C24. 1-(3,4-Dimethoxyphenyl)-3-(dimethylaminomethyl-lene)-2(1H,3H)-indolone; 3-(dimethylaminomethylene)-2(1H,3H)-indolone/3,4-dimethoxyphenyl bromide; not chromatographed; ether; 6%; 164°-167°; (70.35) 70.02, (6.22) 6.06, (8.64) 8.69.

C25. 5-Methoxy-1-(3-chlorophenyl)-3-(dimethylaminomethylene)-2(1H,3H)-indolone; 5-Methoxy-3-(dimethylaminomethylene)-2(1H,3H)-indolone/m-chloroiodobenzene; chloroform; methanol/ether; 9%; 128°-130°; (65.75) 65.27, (5.21) 5.19, (8.52) 8.53.

C26. 1-(3-Dimethylcarbamoylphenyl)-3-(dimethylaminomethylene)-2(1H,3H)-indolone; 3-(dimethylaminomethylene)-2(1H,3H)-indolone/m-iodo-N,N-dimethylbenzamide; 1:1 ethyl acetate:hexane; toluene/pentane; 24%; 180.5°-183°; (70.67) 70.95, (6.38) 6.18, (12.36) 12.35 with 0.25 $H_2O$.

C27. 4-Chloro-1-(3-chlorophenyl)-3-(dimethylaminomethylene)-2(1H,3H)-indolone; 4-chloro-3-(dimethylaminomethylene)-2(1H,3H)-indolone/m-chloroiodobenzene; chloroform; chloroform/ether; 5%; 169°-170°; (61.28) 60.99, (4.23) 4.13, (8.40) 8.40.

C28. 1-(4-Dimethylaminophenyl)-3-(dimethylaminomethylene)-2(1H,3H)-indolone; 3-(dimethylaminomethylene)-2(1H,3H)-indolone/p-bromo-N,N-dimethylaniline; ethyl acetate; ethyl acetate; 32%; 192°-195°; (74.24) 73.92, (6.89) 6.84, (13.67) 13.99.

C29. 1-(4-Methylphenyl)-3-(dimethylaminomethylene)-2(1H,3H)-indolone; 3-(dimethylaminomethylene)-2-(1H,3H)-indolone/p-bromotoluene; ethyl acetate; benzene/pentane; 23%; 135°-137°; (77.67) 77.44, (6.52) 6.54, (10.07) 10.29.

C30. 1-(4-Methylthiophenyl)-3-(dimethylaminomethylene)-2(1H,3H)-indolone; 3-(dimethylaminomethylene)-2-(1H,3H)-indolone/p-methylthiophenyl bromide; ethyl acetate; ethyl acetate/pentane; 32%; 144°-147°; (69.64) 69.45, (5.84) 5.88, (9.03) 8.85.

C31. 6-Chloro-1-(3-chlorophenyl)-3-(dimethylaminomethylene)-2(1H,3H)-indolone; 6-chloro-3-(dimethylaminomethylene)-2(1H,3H)-indolone/m-chloroiodobenzene; ethyl acetate; cyclohexane; 2%; 128°-130°; (61.28) 61.07, (4.23) 4.25, (8.40) 8.37.

C32. 7-Chloro-1-(3-chlorophenyl)-3-(dimethylaminomethylene)-2(1H,3H)-indolone; 7-chloro-3-(dimethylaminomethylene)-2(1H,3H)-indolone/m-chloroiodobenzene; ethyl acetate; methanol/ether; 31%; 172°-175°; (61.28) 61.31, (4.23) 4.31, (8.40) 8.32.

C33. 1-(3-Methyl-4-methoxyphenyl)-3-(dimethylaminomethylene)-2(1H,3H)-indolone; 3-(dimethylaminomethylene)-2(1H,3H)-indolone/p-bromo-o-methylanisole; ethyl acetate; benzene/pentane; 18%; 172°-174°; (74.00) 74.09, (6.54) 6.61, (9.09) 9.08.

C34. 1-(3-Biphenyl)-3-(dimethylaminomethylene)-2-(1H,3H)-indolone; 3-(dimethylaminomethylene)-2(1H,3H)-indolone/3-bromobiphenyl; ethyl acetate; ether; 34%; 131°-133°; (81.15) 81.55, (5.92) 5.93, (8.23) 8.10.

C35. 1-(5-Chloro-2-methoxyphenyl)-3-(dimethylaminomethylene)-2(1H,3H)-indolone; 3-(dimethylaminomethylene)-2(1H,3H)-indolone/p-chloro-o-bromoanisole; ethyl acetate; ether/benzene; 27%; 161°-163°; (65.75) 65.39, (5.21) 5.09, (8.52) 8.39.

C36. 1-(3-Isopropyl-4-methoxyphenyl)-3-(dimethylaminomethylene)-2(1H,3H)-indolone; 3-(dimethylaminomethylene)-2(1H,3H)-indolone/p-bromo-o-isopropyl anisole; ethyl acetate; ether/pentane; 7%; 133°-136°; (74.97) 74.82, (7.19) 7.23, (8.33) 8.10.

C37. 1-(3-Cyanophenyl)-3-(1-methyl-2-pyrrolidinylidene)-2(1H,3H)-indolone; 3-(1-methyl-2-pyrrolidinylidene)-2(1H,3H)-indolone/m-bromobenzonitrile; $CHCl_3$; ether/$CHCl_3$; 16%; 172°-174°; (76.17) 75.86, (5.43) 5.19, (13.32) 13.43.

C38. 1-(3-Dimethylcarbamoylphenyl)-3-(1-methyl-2-pyrrolidinylidene)-2(1H,3H)indolone; 3-(1-methyl-2-pyrrolidinylidene)-2(1H,3H)-indolone/m-iodo-N,N-dimethylaniline; $CHCl_3$; ether/$CHCl_3$; 17%; 170°-172°; (72.20) 72.22, (6.47) 6.38, (11.48) 11.38 with 0.25 $H_2O$.

C39. 6-Chloro-1-(3-chlorophenyl)-3-(1-methyl-2-pyrrolidinylidene)-2(1H,3H)-indolone; 6-chloro-3-(1-methyl-2-pyrrolidinylidene)-2(1H,3H)-indolone/m-chloroiodobenzene; $CHCl_3$; ether/cyclohexane; 43%; 103°-106°; (63.52) 63.54, (4.49) 4.57, (7.80) 7.86.

C40. 1-(4-Chlorophenyl)-3-(1-methyl-2-pyrrolidinylidene)-2(1H,3H)-indolone; 3-(1-methyl-2-pyrrolidinylidene)-2(1H, 3H)-indolone/p-chloroiodobenzene; ethyl acetate; no recrystallization; 48%; 174°-176°; (70.25) 69.93; (5.28) 5.24, (8.63) 8.52.

C41. 1-(3-Chlorophenyl)-3-[1-(p-chlorobenzyl)-2-pyrrolidinylidene]-2(1H,3H)-indolone; 3-[1-(p-chlorobenzyl)-2-pyrrolidinylidene]-2(1H,3H)-indolone/m-chloroiodobenzene; 1:1 ethyl acetate:hexane; ether; 29%; 115°-117°; (67.57) 67.67, (4.76) 4.73, (6.30) 6.35 for 0.5 $H_2O$.

C42. 1-(4-Methoxyphenyl)-3-(1-methyl-2-pyrrolidinylidene)-2-(1H,3H)-indolone; 3-(1-methyl-2-pyrrolidinylidene)-2(1H,3H)-indolone/p-bromoanisole; ethyl acetate; ether; 8.7%; 130°-132°; (74.97) 74.87, (6.29) 6.32, (8.75) 8.73.

PREPARATION C43

1-(3-Fluoro-4-methoxyphenyl)indole

Indole (60 g, 0.51 mole), o-fluoro-p-bromoanisole (112.2 g, 0.547 mole), $K_2CO_3$ (76 g, 0.55 mole) and $Cu_2Br_2$ (14 g) were combined in 600 ml N-methylpyrrolidone and heated at 185°-200° for 48 hours, stirring under $N_2$. The reaction mixture was cooled, poured into ice and water and extracted several times with ethyl acetate. The combined organic layers were washed with $H_2O$, then brine, dried over $MgSO_4$, treated with activated carbon, and concentrated to an oil (148 g). A portion of the oil (25 g) was chromatographed on silica gel (7.5 × 18 cm) eluting with 1:9 $CH_2Cl_2$: hexane, yielding title product as an oil which crystallized on standing in vacuo overnight, 7.2 g, m.p. 65°-67°.

Anal. Calcd. for $C_{15}H_{12}NOF$: C, 74.67; H, 5.02; N, 5.81; m/e 241.

Found: C, 75,27; H, 5.22; N, 6.10; m/e 241.

PREPARATION C44

1-(3-Chloro-4-methoxyphenyl)indole

Indole (14 g, 0.120 mole), o-chloro-p-iodoanisole (34 g, 0.127 mole), $K_2CO_3$ (18 g, 0.13 mole) and $Cu_2Br_2$ (1.0 g) were heated in 200 ml N-methylpyrrolidone at 200° for 24 hours. Crude product was isolated as an oil (27.8 g) as in the preceding preparation then distilled (11.0 g, b.p. 169°–196°/0.3 mm) and finally chromatographed on silica gel with 1:1 CH$_2$Cl$_2$:ethyl acetate as eluant, yielding purified title product as the faster moving component as a viscous oil, 5.23 g; pnmr/CDCl$_3$/delta/TMS: 3.9 (s), 6.6 (d), 6.8–7.7 (m); m/e 259/257

The slower moving component was demethylated title product, 5.0 g; viscous oil; m/e 245/243.

PREPARATION C45

Di-(4-fluorophenyl)amine

A mixture of p-fluoroacetanilide (76.5 g, 0.5 mole), 4-bromofluorobenzene (262.5 g, 1.5 mole), K$_2$CO$_3$ (76 g, 0.55 mole), Cu$_2$Br$_2$ (157.8 g, 0.55 mole) and N-methylpyrrolidone (600 ml) were heated at 175°–180°. After allowing low boiling material to condense off, the mixture was heated at reflux for 7 days. The mixture was cooled to 60° and quenched into a mixture of 2 liters H$_2$O, 600 ml ethylenediamine and 1.2 liters toluene, filtered and the toluene layer separated, back-washed 2×600 ml H$_2$O, treated with activated carbon, dried over MgSO$_4$ and concentrated to oily solids in vacuo. The latter were taken up in 1.5 liters 10% ethanolic KOH, refluxed 18 hours and concentrated in vacuo to an oil. The oil was partitioned between 750 ml H$_2$O and 750 ml. ether. The water layer was washed 2×200 ml ether. The organic layers were combined, back-washed 2×200 ml H$_2$O, treated with activated carbon, dried over MgSO$_4$, reconcentrated to an oil (60.3 g) and distilled to yield purified title product 41.6 g, b.p. 158°–160°/2 mm.

PREPARATION C46

1-(4-Methoxyphenyl)indole

By the method of Preparation C43, p-bromoanisole (140 g, 0.75 mole), indole (60 g, 0.51 mole), K$_2$CO$_3$ (75 g, 0.54 mole) and Cu$_2$Br$_2$ (28 g, 0.1 mole) were converted to title product, purified by distillation, rather than chromatography, 67.7 g, b.p. 150–160/0.4–0.5 mm, which crystallized on storage in the refrigerator, m.p. 52°–54° C.

METHOD D

EXAMPLE D1

1-(3-Hydroxyphenyl)-3-(dimethylaminomethylene)-2(1H,3H)-indolone

Under nitrogen, a solution of title product of Example C1 (0.468 g, 1.59 mmoles) in 5 ml CH$_2$Cl$_2$ was cooled to −78°. Boron tribromide (0.45 ml, 4.77 mmoles) was added. After stirring 20 minutes at −78°, the reaction mixture was allowed to warm to room temperature, stirred 2 hours, diluted with 25 ml. of water and then 20 ml CH$_2$Cl$_2$, stirred 15 minutes, and the pH adjusted to 6–7 with saturated NaHCO$_3$. The aqueous layer was separated and extracted 2×25 ml CH$_2$Cl$_2$. The three organic layers were combined, dried over MgSO$_4$, and concentrated to solids in vacuo, 0.402 g. Recrystallization from CH$_2$Cl$_2$/hexane gave purified title product, 0.320 g, m.p. 200°–203°.

Anal. Calcd. for C$_{17}$H$_{16}$N$_2$O$_2$.1/4H$_2$O: C, 71.69; H, 5.84; 9.84.

Found: C, 71.77; H, 5.72; 9.78.

METHOD E

EXAMPLE E1

1-(3-Ethoxyphenyl)-3-(dimethylaminomethylene)-2(1H,3H)-indolone

Title product of Example D1 (0.28 g, 1.0 mmole) in 2 ml of acetone was stirred under N$_2$ with Na$_2$CO$_3$ (0.21 g, 2 mmoles) for 1 hour. Ethyl iodide (2.28 ml) and 0.5 g Na$_2$CO$_3$ were then added. The mixture was refluxed for 11 hours, cooled, salts removed by filtration and the filtrate stripped of solvent in vacuo. The residue was chromatographed on silica gel (15 cm×3.5 cm), eluting with 1:1 ethyl acetate:hexane. The resulting oil was crystallized from toluene/pentane to yield purified title product; 51.5 mg; 17%; m.p. 99°–102°.

Anal. Calcd. for C$_{19}$H$_{20}$N$_2$O$_2$: C, 74.00; H, 6.54; N, 9.09.

Found: C, 73,88; H, 6.54; N, 8.92.

EXAMPLE E2

4-Bromo-2-chloro-6-methylanisole

4-Bromo-2-chloro-6-methylphenol (50 g, 0.225 mole) and K$_2$CO$_3$ (31.8 g, 0.23 mole) were combined in acetone (300 ml). Dimethyl sulfate (32 ml, 0.34 mole) was added dropwise and the mixture stirred 22 hours at room temperature, filtered and concentrated to an oil in vacuo. The oil was taken up in 250 ml ether, washed 2×2N NaOH, 1× saturated NaHCO$_3$, 2× brine, dried over MgSO$_4$, reconcentrated to an oil and distilled to yield purified title product, 42.9 g, b.p. 122°–124°/0.9 mm, pnmr/CDCl$_3$/delta/TMS:2.3 (s, 3H), 3.8 (s, 3H), 7.3 (q, 2H).

METHOD F

EXAMPLE F1

1-(3-Chlorophenyl)-3-(pyrrolidinomethylene)-2(1H,3H)-indolone

Pyrrolidine (0.42 ml, 5.0 mmoles) was added to a solution of the title product of Example A3 (0.3 g, 1.0 mmole) in 10 ml of ethanol. The mixture was stirred 3 hours and then allowed to stand for 16 hours at 25°. The reaction mixture was evaporated to dryness in vacuo. The residue was triturated with ether and filtered with pentane wash to yield purified title product, 0.253 g; m.p. 108°–112°.

Anal. Calcd. for C$_{19}$H$_{17}$N$_2$OCl: C, 70.25; H, 5.28; N, 8.63; m/e 326/324

Found: C, 70.50; H, 5.36; N, 8.80; m/e 326/324

EXAMPLE F2

1-(3-Chlorophenyl)-3-(morpholinomethylene)-2(1H,3H)-indolone

Title product of Example A3 (0.3 g, 1.0 mmole), morpholine (0.45 ml, 5 mmole) and ethanol (10 ml) were combined and stirred 18 hours at 25°. Additional morpholine (2 ml) was added and the mixture refluxed 4 hours. The reaction mixture was evaporated in vacuo to an oil, chromatographed on silica gel (4.5 cm×18 cm) eluting with ethyl acetate, initially isolating purified title product as an oil which crystallized on standing under ether/pentane, 0.27 g; m.p. 130°–132.5° C.

Anal. Calcd. for C$_{19}$H$_{17}$N$_2$O$_2$Cl: C, 66.96; H, 5.03; N, 8.22; m/e 342/340

Found: C, 66.62; H, 5.07; N, 8.32; m/e 342/340

EXAMPLE F3

1-(3-Chlorophenyl)-3-(aminomethylene)-2(1H,3H)-indolone

Title product of Example A3 (0.3 g, 1 mmole) was stirred with 10 ml of ethanol for 3 minutes and the mixture then perfused with NH$_3$ for 1 hour at 25°, stirred an additional 16 hours, and concentrated to an oil, which crystallized on standing in vacuo. Trituration with pentane gave purified title product, 0.25 g, m.p. 141°–143°.

Anal. Calcd. for $C_{15}H_{11}N_2OCl.1/4H_2O$: C, 65.46; H, 4.21; N, 10.18; m/e 272/270

Found: C, 65.22; H, 4.40; N, 10.29; m/e 272/270

EXAMPLES F4–F10

Method F (Examples F1–F3) was further employed to prepare the following additional compounds. Listed sequentially are: example number; product name; starting materials; chromatography eluant; crystallization solvent(s); yield; m.p.; C, H and N microanalyses (calculated) found.

F4. 1-(3-Chlorophenyl)-3-(benzylaminomethylene)-2(1H,3H)-indolone; title product Example A3/benzyl amine; no chromatography; ethanol; 90%; 97°–99°; (73.32) 73.65, (4.75) 4.94, (7.77) 7.98.

F5. 1-(3-Chlorophenyl)-3-(methylaminomethylene)-2(1H,3H)-indolone; title product Example A3/methylamine; no chromatography; ethanol; 73%; 151.5°–153°; (67.49) 67.75, (4.60) 4.77, (9.84) 9.82.

F6. 1-(3-Chlorophenyl)-3-[(N-methyl-N-benzylamino)methylene]-2(1H,3H)-indolone; title product of Example A3/N-methylbenzylamine; ethyl acetate/hexane; ethyl acetate/hexane; 3%; 118°–120°; (71.96) 71.70, (5.25) 5.22, (7.30) 7.26 with 0.5 H$_2$O.

F7. 6-Chloro-1-phenyl-3-(aminoethylidene)-2(1H,3)-indolone; first title product of Example A2/ammonia; no chromatography; ethanol; 29%; 170°–172.5°; (67.49) 67.21, (4.60) 4.62, (9.84) 9.77.

F8. 6-Chloro-1-phenyl-3-pyrrolidinoethylidene-2(1H,3H)-indolone; first title product of Example A2/pyrrolidine; ethyl acetate; ether/pentane; 28%; 128°–131°; (70.89) 70.75, (5.65) 5.65, (8.27) 8.32.

F9. 1-(3-Chlorophenyl)-3-(piperidinomethylene)-2(1H,3H)-indolone; title product of Example A3/piperidine; ethyl acetate/hexane; ethyl acetate/hexane; 62%; 153°–155°; (70.89) 70.49, (5.65) 5.72, (8.27) 8.32.

F10. 1-(3-Chlorophenyl)-3-(1-aminoethylidene)-2(1H,3H)-indolone; second title product of Example A2/NH$_3$; no chromatography; ethanol; 70%; 200°–202°; (67.49) 67.37, (4.60) 4.67, (9.84) 9.95.

METHOD G

EXAMPLE G1

1-Phenyl-3-[1-(1-imidazolyl)methylene]-2(1H,3H)-indolone

To 1-phenyl-3-(hydroxymethylene)-2(1H,3H)-indolone (1.0 g, 4.2 mmoles) suspended in 25 ml benzene was added carbonyldiimidazole (0.75 g, 4.6 mmoles). The mixture was stirred 16 hours at room temperature and title product recovered by filtration, 0.39 g, m.p. 158°–161°.

Anal. Calcd. for $C_{18}H_{13}N_3O.\frac{1}{2}H_2O$: C, 72.96; H, 4.76; N, 14.18; m/e 287

Found: C, 72.81; H, 4.71; N, 14.22; m/e 287

EXAMPLE G2

1-(3-Chlorophenyl)-3-[1-(1-imidazolyl)-methylene]-2(1H,3H)-indolone

By the procedure of Example G1, substituting toluene for benzene, 1-(3-chlorophenyl)-3-(hydroxymethylene)-2(1H,3H)-indolone was converted to present title product in 11% yield, m.p. 164°–166°.

Anal. Calcd. for $C_{18}H_{12}ClN_3O$: C, 67.19; H, 3.76; N, 13.06.

Found: C, 67.12; H, 4.04; N, 13.21.

METHOD H

EXAMPLE H1

1-(3-Chlorophenyl)-3-(diethylaminomethylene)-2(1H,3H)-indolone 1-(3-Chlorophenyl)-3-(ethoxymethylene)-2(1H,3H)-indolone (0.15 g, 0.5 mmole), diethylamine (5 ml, 48 mmole) and ethanol (30 ml) were combined and stirred 24 hours at 25°. The reaction mixture was concentrated in vacuo to an oil. The oil was taken up in ethyl acetate, washed with H$_2$O and then brine, dried over MgSO$_4$ and evaporated to yield title product which crystallized on cooling and trituration with ether/pentane, 96 mg. m.p. 74°–75.5°.

Anal. Calcd. for $C_{19}H_{19}N_2OCl$: C, 69.92; H, 5.86; N, 8.57; m/e 328/326

Found: C, 69.70; H, 5.85; N, 8.63; m/e 328/326

METHOD J

PREPARATION J1

1-(3-Chlorophenyl)-2(1H,3H)-indolone; 4-Chloro-1-phenyl-2(1H,3H)-indolone; and 6-Chloro-1-phenyl-2(1H,3H)-indolone N-(3-Chlorophenyl)-alpha-chloroacetanilide (63.1 g) and aluminum chloride (70.2 g) were heated for 15 minutes at 180°–200°, cooled to 80°, poured over 500 g ice/250 ml conc. HCl and extracted 3×500 ml CH$_2$Cl$_2$. The combined organic layers were washed 2× saturated NaHCO$_3$ and then 2× brine, dried over MgSO$_4$, treated with activated carbon and evaporated in vacuo to solids (54.2 g). The solids were chromatographed on silica gel (7.5×30 cm) with 19:1 hexane:ethyl acetate as eluant. Faster moving fractions (8–11) gave the 4-chloro-1-phenyl isomer, 2.6 g, m.p. 87°–90°. Middle fractions (13–14) gave the 1-(3-chlorophenyl) isomer, 22.1 g, m.p. 110°–112.5°. Fractions (15–18) containing a mixture of 1-(3-chlorophenyl) and 6-chloro-1-phenyl isomer, 19.7 g, were retained for rework or used in further processing e.g., in Example A2. Slowest fractions (19–21) gave pure 6-chloro-1-phenyl isomer, 3.6 g, m.p. 116°–118.5°.

PREPARATION J2

1-(3-Fluorophenyl)-2(1H,3H)-indolone; and 6-Fluoro-1-phenyl-2(1H,3H)-indolone A mixture of N-(3-fluorophenyl)-alpha-chloroacetanilide (5.3 g, 0.02 mole) and AlCl$_3$ (5.6 g, 0.042 mole) was heated in an open beaker (internal temperature 180°–190°) until gas evolution ceased. After 10 minutes additional heating at this temperature, the reaction mixture was treated with ice chips, yielding a brown gum, and then extracted with ether. Mixed products were then isolated as an oil from the organic extract according to the preceding example (4.7 g), chromatographed on 250 g silica gel with 5:1 hexane:ethyl acetate as eluant, collecting 40 ml fractions. Fractions 90-130 gave the 1-(3-fluorophenyl) isomer, 1.3 g, m.p. 94°-96°. Middle fractions gave mixed isomers; and fractions 170-190 gave the 6-fluoro-1-phenyl isomer, 0.41 g, m.p. 63°-67°.

METHOD K

PREPARATION K1

N-(3-Chlorophenyl)-alpha-chloroacetanilide

N-(3-Chlorophenyl)aniline (25.1 g, 0.123 mole) and chloroacetyl chloride (19.6 ml, 0.246 mole) were refluxed in toluene (100 ml) for 4 hours, then stripped of toluene and excess acid chloride in vacuo to yield an oil which crystallized on scratching. Recrystallization from ethanol/$H_2O$ gave purified title product, 32.6 g, m.p. 94°-96.5°.

PREPARATION K2

N-(3-Fluorophenyl)-alpha-chloroacetanilide

N-(3-Fluorophenyl)aniline (7.02 g, 0.0375 mole) and chloroacetyl chloride (3.3 ml, 0.0412 mole) were refluxed in benzene (50 ml) for 3 hours, then evaporated in vacuo to solids and the solids triturated with pentane and ether to yield purified title product, 8.69 g, m.p. 115°-117°.

METHOD L

PREPARATION L1

1-(3-Fluoro-4-methoxyphenyl)-2(1H,3H)-indolone 1-(3-Fluoro-4-methoxyphenyl)indole (7.0 g, 0.029 mole), N-chlorosuccinimide (98%, 4.14 g, 0.0304 mole) and $CH_2Cl_2$ (200 ml) were combined and stirred 2 hours at 25° C., producing a solution which was evaporated in vacuo to a semisolid. The latter was diluted with 120 ml $CH_3CO_2H$ and warmed to 70°. $H_3PO_4$ (85%, 31.3 ml) was added in one portion, the mixture was refluxed 1 hour, cooled, basified with saturated $Na_2CO_3$ and extracted 4×100 ml ethyl acetate. The organic layers were combined, dried over $MgSO_4$, and evaporated in vacuo to solids (7.9 g). Chromatography on silica gel, (7.5×15 cm) eluting with $CH_2Cl_2$ in 1 liter fractions gave, on evaporation of combined fractions 4-13, purified title product, 3.8 g, m.p. 133°-136°.

PREPARATION L2

1-(3-Chloro-4-methoxyphenyl)-2(1H,3H)-indolone

Using 3:2 hexane:ethyl acetate as eluant on chromatography, the procedure of the preceding preparation was used to convert 1-(3-chloro-4-methoxyphenyl)indole (0.93 g) to present title product, 0.71 g, m.p. 165°-167°.

PREPARATION L3

1-(4-Methoxyphenyl)-2(1H,3H)-indolone

Omitting the final chromatography, but triturating the crude product three times with ether, 1-(4-methoxyphenyl)indole (18.1 g, 81 mmoles) was converted to title product, 12.0 g, m.p. 115°-117° C., pnmr/$CDCl_3$/TMS/delta: 3.65 (s, 2H), 3.8 (s, 3H), 6.6-7.4 (m, 8H).

MISCELLANEOUS METHODS

EXAMPLE M1

1-(3-Fluoro-4-methoxyphenyl)-3-(2-pyrrolidinylidene)-2(1H,3H)-indolone

Title product of Preparation L1 (1.0 g, 3.9 mmoles) and 2-ethoxy-1-pyrroline (1.3 g, 11.7 mmoles, Chem. Pharm. Bull. 17, pp. 2230-2239, 1969) were combined in 10 ml toluene and refluxed for 20 hours. Additional 2-ethoxy-1-pyrroline (2 ml) was added and reflux continued for 2 hours. The reaction mixture was cooled, diluted with ice water and ethyl acetate, and the organic layer separated, washed with saturated $NaHCO_3$, $H_2O$ and brine, dried over $MgSO_4$ and evaporated in vacuo to crude title product, solids, 1.5 g. Crude product was chromatographed on silica gel, 4.5×18.0 cm column, with ethyl acetate as eluant monitoring by tlc. Later fractions, Rf 0.1 (1:1 ethyl acetate:hexane, were combined, evaporated to solids and recrystallized from ethyl acetate to yield purified title product, 0.472 g, m.p. 169°-171°C.

Anal. Calcd. for $C_{19}H_{17}N_2O_2F$: C, 70.35; H, 5.28; N, 8.64.

Found: C, 70.31; H, 5.52; N, 8.56.

A second crop, 0.097 g, m.p. 168°-170° C., was obtained from mother liquor.

The method of Example M1 was further employed to prepare the following additional compounds. Listed in sequence are example number; name of product; starting materials; chromatography eluant; crystallization solvent(s); yield; m.p.; C, H and N microanalyses (calculated) found.

M2. 1-Phenyl-3-(2-perhydroazepinylidene)-2(1H,3H)-indolone; 1-phenyl-2(1H,3H)-indolone/3,4,5,6-tetrahydro-7-methoxy(2H)azepine; no chromatography; benzene/pentane; 46%; 144°-146°; (78.91) 78.59, (6.62) 6.60, (9.21) 9.15.

M3. 1-(3-Chlorophenyl)-3-(2-perhydroazepinylidene)-2(1H,3H)-indolone and 6-chloro-1-(3-chlorophenyl-3-(2-perhydroazepinylidene)-2(1H,3H)-indolone; mixture of 1-(3-chlorophenyl)-2(1H,3H)-indolone and 6-chloro-1-phenyl-2(1H,3H)-indolone/3,4,5,6-tetrahydro-7-methoxy(2H)azepine; ethyl acetate/hexane; no recrystallization; 44% and 9%; 144°-146° and 158°-161°; (70.89) 71.20 and 70.76; (5.65) 5.60 and 5.56; (8.27) 8.30 and 8.10, respectively.

PREPARATION M4

1-(4-Fluorophenyl)-5-fluoroisatin

Oxalyl chloride (9.62 ml, 0.11 mole) was dissolved in 45 ml $CH_2Cl_2$. A solution of di-(4-fluorophenyl)-amine (19.7 g, 0.096 mole) in 145 ml $CH_2Cl_2$ was added over 15 minutes; the temperature rose from 23° to 28°. After stirring 1 hour, $AlCl_3$ (40.8 g) was added portionwise over 15 minutes; the temperature rose from 20° to 30°, and was kept less than 30° by cooling. After stirring for 10 minutes, the reaction mixture was added to 250 ml ethyl acetate and 500 ml ice and water (the temperature rose to 30° C.). The aqueous layer was washed 2×250 ml ethyl acetate. The organic layers were combined, back-washed 1×400 ml $H_2O$, dried over $MgSO_4$, evaporated to solids and triturated with 100 ml 1:1 ether:hexane to recover title product, 19.9 g, m.p. 180°-190°, tlc Rf 0.55 (1:1 ether:hexane).

PREPARATION M5

5-Fluoro-1-(4-fluorophenyl)-2(1H,3H)-indolone

A mixture of title product of the preceding Preparation (4.8 g) KOH (85%, 3 g), hydrazine hydrate (64%, 50 ml) and diethyleneglycol was stirred and slowly heated to 125° (exothermic reaction was noted during warming to 60°). After stirring 16 hours at 125°, the mixture was heated to 140° for 1 hour, then cooled to 50°, poured into 300 ml H$_2$O, acidified with conc. HCl, and extracted 2× with CH$_2$Cl$_2$. The organic extracts were combined, dried over MgSO$_4$ and evaporated in vacuo to a gum. The gum was taken up in ether, a small amount of intermediate 3-hydrazone recovered by filtration, and the filtrate evaporated to yield title product, recrystallized from isopropanol, 2.79 g; m.p. 135°–140°; tlc Rf 0.5 (1:1 ether:hexane); m/e 245.

PREPARATION M6

1-(3-Chlorophenyl)-3-(ethoxymethylene)-2(1H,3H-indolone 1-(3-Chlorophenyl)-2(1H,3H)-indolone (2.4 g, 0.01 mole) and triethyl orthoformate (8.3 ml, 0.05 mole) were combined and heated at 150±10° for 18 hours. An additional 20 ml of the orthoformate were added and heating continued 2 hours. The reaction mixture was cooled to 25°, diluted with ether, washed with H$_2$O and then brine, dried over MgSO$_4$, concentrated in vacuo to oily solids, and triturated with pentane to yield solids (4.2 g). The solids were chromatographed on silica gel (7.5×15 cm) with 4:1 hexane:ethyl acetate as eluant to yield purified title product, 0.5 g; m.p. 132°–134°; m/e 310/299.

PREPARATION M7

1-Phenyl-3-(hydroxymethylene)-2(1H,2H)-indolone

Potassium t-butoxide (1.63 g, 14.5 mmoles) and 5 ml absolute ethanol were heated to 80°. 1-Phenyl-2(1H,3H)-indolone (2.09 g, 10 mmoles) was added, followed by ethyl formate (1.09 ml, 13.5 mmoles). The mixture was heated 5 minutes, cooled to 25°, and the nearly solid mass diluted with 50 ml H$_2$O and crushed ice, acidified to pH 3 with 3N HCl and title product recovered by filtration, 2.2 g, m.p. 192°–195°; m/e 237. cf J. Prakt. Chem. 135:345–360 (1932); J. Med. Chem. 8:637 (1965).

PREPARATION M8

1-(3-Chlorophenyl)-3-(hydroxymethylene)-2(1H,3H)-indolone

By the method of the preceding Example, 1-(3-chlorophenyl)-2(1H,3H)-indolone (1.22 g, 5 mmoles) was converted to title product 1.21 g, m.p. 175°–178° C., m/e 273/271.

We claim:
1. A compound of the formula

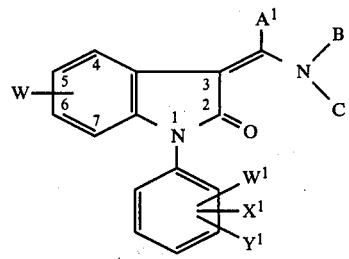

wherein
A$^1$ and B together are 1,3-propylene, 1,4-butylene or 1,5-pentylene;
C is hydrogen, (C$_1$–C$_2$)alkyl, phenyl or benzyl;
W is hydrogen, (C$_1$–C$_2$)alkyl, (C$_1$–C$_2$)alkoxy, chloro, or fluoro; and
W$^1$, X$^1$ and Y$^1$ are each independently hydrogen, (C$_1$–C$_2$)alkyl, (C$_1$–C$_2$)alkoxy, (C$_1$–C$_2$)alkylthio, bromo, chloro, fluoro, trifluoromethyl, hydroxy, formyl, carboxamido, (C$_1$–C$_2$)alkylcarboxamido, di(C$_1$–C$_2$)alkylcarboxamido, cyano, nitro, amino, (C$_1$–C$_2$)alkylamino or di(C$_1$–C$_2$)alkylamino.

2. A compound of claim 1 wherein A$^1$ and B together are 1,3-propylene.

3. A compound of claim 2 wherein C is methyl and W$^1$ is hydrogen.

4. The compound of claim 3 wherein W and Y$^1$ are hydrogen and X$^1$ is 3-methoxy.

5. The compound of claim 3 wherein W is hydrogen, X$^1$ is 3-chloro and Y$^1$ is 4-methoxy.

6. The compound of claim 3 wherein W and X$^1$ are hydrogen and Y$^1$ is 4-methoxy.

7. The compound of claim 3 wherein W is 6-chloro and X$^1$ and Y$^1$ are hydrogen.

8. A compound of claim 3 wherein W, W$^1$ and Y$^1$ are hydrogen and X$^1$ is 3-chloro.

9. The compound of claim 7 wherein A$^1$ and B together are 1,3-propylene and C is benzyl.

10. The compound of claim 7 wherein A$^1$ and B together are 1,3-propylene and C is methyl.

11. The compound of claim 7 wherein A$^1$ and B together are 1,4-butylene and C is methyl.

* * * * *